(12) United States Patent
Frielinghaus et al.

(10) Patent No.: US 11,530,984 B2
(45) Date of Patent: Dec. 20, 2022

(54) FOOD ANALYSIS DEVICE

(71) Applicant: Vorwerk & Co. Interholding GmbH, Wuppertal (DE)

(72) Inventors: Robert Frielinghaus, Bochum (DE); Hendrik Koetz, Wetter (DE)

(73) Assignee: Vorwerk & Co. Interholding GmbH

( * ) Notice: Subject to any disclaimer, the term of this patent is extended or adjusted under 35 U.S.C. 154(b) by 0 days.

(21) Appl. No.: 16/293,123

(22) Filed: Mar. 5, 2019

(65) Prior Publication Data

US 2019/0277757 A1 Sep. 12, 2019

(30) Foreign Application Priority Data

Mar. 6, 2018 (EP) ..................... 18160090

(51) Int. Cl.
*G01N 21/3577* (2014.01)
*G01N 21/25* (2006.01)
(Continued)

(52) U.S. Cl.
CPC ....... *G01N 21/3577* (2013.01); *B01F 35/213* (2022.01); *B01F 35/2209* (2022.01);
(Continued)

(58) Field of Classification Search
CPC ............. G01N 21/3577; G01N 21/359; G01N 21/255; G01N 33/02; B01F 15/00207; B01F 15/00253; B01F 15/065; B01F 2015/062; B01F 7/162; G01J 3/0218; G01J 3/0256; G01J 3/0291
See application file for complete search history.

(56) References Cited

U.S. PATENT DOCUMENTS 7,075,645 B2 * 7/2006 Gehrlein ................... B01F 3/02
356/328
7,842,985 B2 * 11/2010 Lim .................. H01L 27/14603
257/233
(Continued)

FOREIGN PATENT DOCUMENTS

DE 29810164 U1 10/1998
WO 2017051424 A1 3/2017
WO 2018015951 A1 1/2018

OTHER PUBLICATIONS

European Patent Office, "EPA Form 2008, EPA Form 2906", App. No. 18160090.9, dated Oct. 21, 2021, 15 pages.

*Primary Examiner* — Violeta A Prieto
(74) *Attorney, Agent, or Firm* — Barnes & Thornburg LLP

(57) ABSTRACT

The present disclosure relates to a spectrometer comprising a spectral decomposition device and a radiation detector. These components are configured such that the spectral decomposition device can break up an incident electromagnetic measuring radiation into components in a wavelength-dependent manner. The radiation detector can measure the intensity of at least one of these components. The spectrometer is configured such that the spectrometer transmits analysis information from the analysis of a food or of a food component to a food preparation device and/or outputs it to the user via an output device. The present disclosure further relates to a system including a control device as well as to a method. In this way, a reproducible cooking result as well as an output of the nutritional values and the actual energy content of the prepared food can be made possible.

15 Claims, 2 Drawing Sheets

Figure 1:
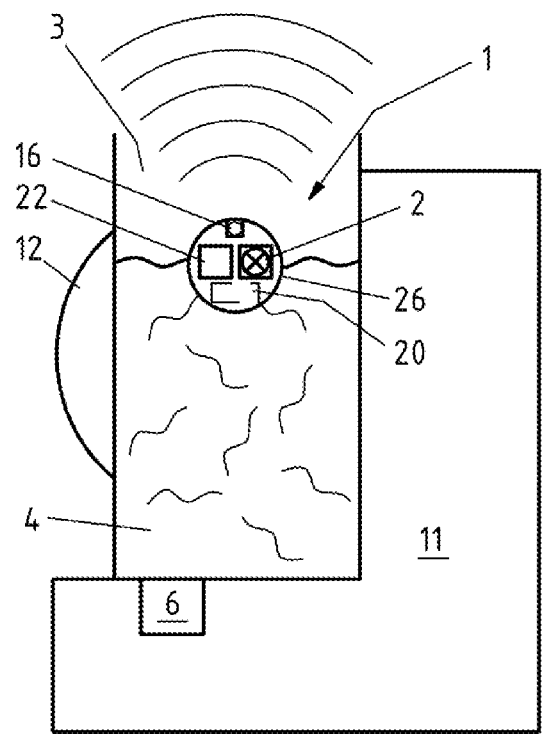

(51) Int. Cl.
  *G01N 33/02*   (2006.01)
  *G01J 3/02*    (2006.01)
  *B01F 35/92*   (2022.01)
  *B01F 35/213*  (2022.01)
  *B01F 35/22*   (2022.01)
  *G01N 21/359*  (2014.01)
  *B01F 27/808*  (2022.01)
  *B01F 35/90*   (2022.01)

(52) U.S. Cl.
  CPC ............ *B01F 35/92* (2022.01); *G01J 3/0218* (2013.01); *G01J 3/0256* (2013.01); *G01J 3/0291* (2013.01); *G01N 21/255* (2013.01); *G01N 33/02* (2013.01); *B01F 27/808* (2022.01); *B01F 2035/99* (2022.01); *G01N 21/359* (2013.01)

(56) References Cited

U.S. PATENT DOCUMENTS

| | | | |
|---|---|---|---|
| 8,967,851 B1* | 3/2015 | Kemeny | G01N 21/359 366/143 |
| 11,067,498 B2* | 7/2021 | Frielinghaus | A23L 5/15 |
| 2005/0223905 A1* | 10/2005 | Ghiraldi | G01N 33/02 99/342 |
| 2007/0188753 A1 | 8/2007 | Merrill et al. | |
| 2013/0207156 A1* | 8/2013 | Moosburger | H01L 27/15 438/33 |
| 2013/0284908 A1* | 10/2013 | Rossi | G01J 1/0411 250/221 |
| 2014/0116158 A1* | 5/2014 | Minteer | B01L 3/502 73/863.01 |
| 2015/0327742 A1 | 11/2015 | Strang | |
| 2016/0067866 A1 | 3/2016 | Sekar et al. | |
| 2016/0161519 A1* | 6/2016 | Minteer | G01N 27/02 435/5 |
| 2017/0038305 A1 | 2/2017 | Catching et al. | |
| 2019/0056315 A1* | 2/2019 | Kinrot | G01N 21/3151 |
| 2019/0142222 A1* | 5/2019 | Resende | A47J 43/0716 426/231 |
| 2019/0157470 A1* | 5/2019 | Send | G01S 7/4816 |
| 2019/0191930 A1* | 6/2019 | Yan | A47J 43/046 |
| 2019/0261805 A1* | 8/2019 | Yan | A47J 43/046 |
| 2019/0277754 A1* | 9/2019 | Frielinghaus | A23L 5/30 |
| 2020/0152312 A1* | 5/2020 | Connor | G06K 9/00335 |

* cited by examiner

FOOD ANALYSIS DEVICE

PRIORITY CLAIM

This application claims priority to European Application No. 18160090.9, filed Mar. 6, 2018, which application is hereby incorporated in its entirety herein.

FIELD OF THE DISCLOSURE

The present disclosure relates to a spectrometer comprising a spectral decomposition device and a radiation detector, which are configured such that the spectral decomposition device can break up an incident electromagnetic measuring radiation into components in a wavelength-dependent manner, and the radiation detector can measure the intensity of at least one of these components. The present disclosure further relates to system and a method.

BACKGROUND

To date, the nutritional values and the energy content of an, in particular self-prepared, food are gathered from generically determined recipe information or manually determined based on the ingredients by means of weighing and nutritional value tables. Therefore, the information about the nutritional values and the energy content of a food prior to consumption is inaccurate or difficult to determine. In addition, even based on the ingredients, reliable conclusions generally cannot be drawn with respect the prepared food, due to processes of change in the food or individual food components during cooking.

Particularly in private households, an increasing interest in a healthy diet, high-quality foods and a precise knowledge of the actual nutritional values of self-prepared foods can be observed.

SUMMARY

It is the object of the present disclosure to provide a solution that takes into account the problems described above.

A spectrometer, a system, and a method according to the present disclosure serve for achieving the object. Advantageous embodiments are apparent from the description and drawings provided.

A spectrometer comprising a spectral decomposition device and a radiation detector serves for achieving the object, which are configured such that the spectral decomposition device can break up an incident electromagnetic measuring radiation into components in a wavelength-dependent manner, and the radiation detector can measure the intensity of at least one of these components.

The spectrometer is configured such that the spectrometer transmits analysis information from the analysis of a food or of a food component to a food preparation device and/or outputs it to the user via an output device.

The analysis of a food or of a food component, i.e. an ingredient, for example, means the identification and/or quantification of a food component, a nutrient, a nutrition component or other ingredient substance of the food or of the food component, and/or the determination of the energy content or of a state of the food or the food component. The nutrients include the main nutrients, i.e. protein, fat and carbohydrates or, for example, vitamins. Nutrition components are, for example, water or cholesterol. Other ingredient substances may include sodium nitride ($NaNO_2$), for example. A state may be a browning level during cooking. The energy content is generally specified in units of kcal. Generally, food may be solid or liquid. A food component, taken by itself, may also be a food, such as milk or drinking water.

Analysis information may be a measurement signal of the radiation detector or an analytical result. Analysis information may have an analog or digital form.

A food preparation device is capable of preparing, i.e. heating, stirring, blending and/or chopping, a food. A food preparation device may be, for example, an oven, a cooking machine or an electric food processor, particularly with a tool for blending and/or chopping, which may optionally also be capable of heating.

By means of a spectrometer that transmits analysis information from the analysis of a food or a food component to a food preparation device, the recipe and/or the preparation parameters of the food preparation device can be monitored and dynamically adapted, namely prior to and during the preparation of the food. So far, information of this kind was not known to a food preparation device. By using a spectrometer, information of this type can be made accessible to the food preparation device, and a particularly reproducible cooking result can thus be made possible. The use of a large number of individual sensors for detecting, in each case, a certain substance or a certain state, such as the browning level by means of camera technology, alcohol concentrations by means of refractometers or water content by means of differential thermometry, may be dispensed with.

By means of a spectrometer that outputs analysis information from the analysis of a food or a food component to the user via an output device, the user can visually receive accurate information about the nutritional content, the energy content, or possible undesired ingredient substances, which are actually present in the ingredients or the food that is ready for consumption. Furthermore, the user can be notified directly by the spectrometer, by an acoustic signal, if a desired condition of the food has been reached during preparation, for example. Alternatively or additionally, the user is finally able to have analysis information output via a data interface for his own analysis. A recipe-based estimation of the nutrients and the energy content using nutrient and calorie tables can be dispensed with, and detailed information about the actually present food or food component can be obtained.

In one embodiment, the spectrometer is portable. Portable means capable of being carried with one hand. Preferably, one hand is sufficient also for operation and handling. A particularly convenient and simple use for the user can thus be ensured. Moreover, a bracket with a particularly simple and compact design can serve for temporarily fixing it to a kitchen appliance or oven, in order for it to be incorporated into the monitoring of the preparation process. In particular, a portable spectrometer has a weight of less than one kilogram, preferably less than half a kilogram, particularly preferably a weight of less than 300 g. In order to fit into a hand particularly comfortably, the portable spectrometer preferably has the shape of a remote control, i.e. elongate with at least twice and/or at most five times the length as compared to the width and/or a thickness, which corresponds to at most half or a quarter of the width. Alternatively or additionally, the portable spectrometer may have a rounded, sphere-like or spherical shape in order to be particularly rugged and space-saving for being conveyed towards a food. Preferably, a portable spectrometer comprises a rechargeable battery for being supplied with electrical energy.

In one embodiment, the spectrometer is encapsulated. "Encapsulated" means encased in a moisture- and temperature-resistant manner by a capsule-like housing. Thus, a spectrometer can be conveyed towards a food prior to, during or subsequent to preparation. Encapsulation reduces the risk in using a rechargeable battery when the spectrometer is placed in a food, particularly during preparation.

In one embodiment a capsule-like housing, which has a biocompatible coating or outer wall, is provided for encapsulating the spectrometer. "Biocompatible" means that the consumption of abraded matter or the material of the coating or of the outer wall itself is harmless, i.e. without any appreciable health risks. Thus, a health risk by placing the spectrometer in a food prior to, during or subsequent to preparation can thus be avoided or at least significantly reduced.

In one embodiment, the spectrometer comprises a data interface for wirelessly transmitting the analysis information. The analysis information can be transmitted particularly simply, hygienically and conveniently in this manner, even if the spectrometer is conveyed towards a food prior to, during or subsequent to preparation. However, the ease of operation in portable usage, for example for analyzing an ingredient in a bowl on the table distant from the food preparation device, may also be increased in this manner. In particular, the data interface supports Bluetooth or wireless LAN.

In one embodiment, the spectrometer comprises a beam source for emitting an excitation radiation. "Excitation radiation" means electromagnetic radiation for introducing energy into the food or food component to be analyzed. A wide-band beam source, e.g. a Globar, a quartz halogen lamp or a high-pressure mercury lamp, with a spectrum known through reference measurement or calibration, is preferably provided. Alternatively or additionally, a diode laser is used as a beam source. A particularly precise analysis can be obtained using a beam source.

If a beam source is provided, the excitation radiation, i.e. photons, from the beam source is incident upon the food to be analyzed. There, the molecules are excited by this incident or introduced energy. Depending on the food, its properties or state, the excitation radiation is reflected, absorbed or transmitted by the food in certain fractions of the incident excitation radiation. In particular, the reflected radiation and/or the transmitted radiation are used as the measuring radiation to be captured by the radiation detector. Preferably, the reflected radiation is used as the measuring radiation. The term "measuring radiation" means the radiation from the food or a food component to be analyzed for analyzing the food.

Preferably, the beam source emits an excitation radiation in the infrared range, particularly preferably in the near infrared range (NIR). A food or food component can thus be analyzed particularly reliably. In particular, the infrared radiation includes near infrared radiation (NIR) with a wavelength range of 780 nm to 1,400 nm, short-wavelength infrared radiation (SWIR) in the range of 1,400 nm to 3,000 nm, mid-wavelength infrared radiation (MWIR) in the range from 3,000 nm to 8,000 nm, long-wavelength infrared (LWIR) in the range from 8,000 to 15,000 nm and/or far infrared radiation (FIR) in the range from 15,000 nm to 1,000,000 nm. A particularly large number of substances and states that can be analyzed can thus be made possible.

In one embodiment, the spectral decomposition device and the radiation detector are configured such that the measuring radiation in the infrared range or near infrared range can be captured for the analysis. A food can thus be analyzed particularly reliably.

A radiation detector is a preferably electronic or optoelectronic device for measuring the intensity of incident electromagnetic radiation, i.e. the measuring radiation or a component of the measuring radiation. A measurement signal correlating with the intensity of a component of the measuring radiation is provided by the radiation detector. "Measuring radiation" is the electromagnetic radiation from an object, i.e. a food or food component, which is intended for spectroscopic analysis.

A spectral decomposition device is a preferably optical device, which is capable of diverting or guiding an electromagnetic measuring radiation into a different direction depending on the wavelength, in particular by means of dispersion and/or refraction, so that a first component of the measuring radiation with a first wavelength hits a first area of the radiation detector, and a second component of the measuring radiation with a second wavelength differing from the first wavelength hits a second area of the radiation detector. In one embodiment, the spectral decomposition device is a prism. This enables spectral decomposition with a particularly small construction space and production expenditure. Alternatively or additionally, a grating or an interferometer can be provided as the spectral decomposition device.

In one embodiment, the radiation detector comprises only a single detector unit, at least two separate detector units and/or at most thirty, preferably at most fifteen, separate detector units. If only a single detector unit is included, a CCD sensor is preferably provided as the detector unit in order to cover a particularly broad wavelength range with a particularly low production expenditure. A CCD sensor has a matrix of pixels, wherein each pixel is capable of converting the intensity of an incident electromagnetic radiation or of a component of the measuring radiation into a measurement signal correlating with the intensity. In particular, the pixels are rectangular, square or polygonal, preferably with an edge length of at least 1 μm and/or at most 50 μm. Preferably, the pixel matrix is produced by micro-structuring a metal-insulator-semiconductor layer structure. If the radiation detector includes at least two separate detector units, i.e. no pixels of a CCD sensor, a separate photodiode is respectively used for each of the detector units, which can be positioned and fixed independently of another photodiode. A photodiode is capable of converting the intensity of an incident electromagnetic radiation or of a component of the measuring radiation into a measurement signal correlating with the intensity. Alternatively, the use of only a single photodiode is also possible if only a single detector unit is provided, wherein the single photodiode is then driven along the measuring radiation, which has been deflected according to its wavelength, so that a measured intensity can be associated with a wavelength based on the position of the measurement.

In one embodiment, a photodiode or a CCD sensor is used, which is capable of acquiring infrared radiation (IR), preferably near infrared radiation (NIR). "Acquiring" means that an intensity of an incident electromagnetic radiation can be converted into a measurement signal correlating with the intensity. Thus, a particularly precise analysis of a food or a food component is obtained. In one embodiment, mercury cadmium telluride is used as the semiconductor material for the photodiode or the CCD sensor in order to be able to capture measuring radiation in the NIR, SWIR, MWIR and LWIR ranges. Alternatively or additionally, indium gallium arsenide or lead(II) sulfide is used in order to be able to capture measuring radiation in the NIR and SWIR ranges.

In one embodiment, separate detector units are positioned at such locations of the radiation detector at which a component of the measuring radiation is respectively incident, whose wavelength, in connection with an intensity threshold or an intensity range, defines a spectroscopic fingerprint for a certain food component, nutrient, nutrition component, ingredient substance or state. A particularly compact structure, which can be manufactured with particularly little effort and is tailor-made for the analysis of a food or a food component, is made possible. Because the main nutrients, for example, have peaks at certain wavelengths in a spectrometric measurement, i.e. have a spectroscopic fingerprint, a classification and identification can by carried out by comparing the measurement signals to stored reference values or by monitoring wavelength-dependent intensity thresholds.

In one embodiment, the spectrometer comprises an optical fiber or an optical coupling interface for coupling an optical fiber. An optical fiber is capable of guiding electromagnetic radiation, particularly in the NIR range. The optical fiber, which is preferably made from glass or plastic, permits bending. By using an optical fiber, the spectrometer can be placed at any position in the vicinity of a food preparation device or, temporarily, be manually mechanically attached to a bracket on the food preparation device, so that the optical fiber can be directed towards the food or a food component from there. In particular, the optical fiber may be routed through an opening in a lid of the food preparation space or coupled to an optical coupling interface on a container or tool of the food preparation device in order to be directed toward the food. Preferably, two optical fibers are provided, of which one optical fiber is in each case connected to the beam source and the radiation detector in an optically conductive manner. Thus, excitation and measurements can be carried out in a targeted manner.

In one embodiment, an optical combiner is provided, which is configured such that the excitation radiation can be guided through the optical fiber and an additional optical fiber, or the measuring radiation can be guided through the optical fiber and an additional optical fiber. An optical combiner is a Y-distribution device. Thus, either can measuring radiation from the optical fiber and the additional optical fiber be guided to the same radiation detector, or excitation radiation from only a single beam source can be guided through the optical fiber and the additional optical fiber.

With an optical combiner, it can be made possible that an additional optical fiber can be connected or coupled to the beam source or the radiation detector in addition to the optical fiber. Thus, a food can be analyzed at two different locations. Furthermore, a food can be analyzed within, and a food or a food component outside, a food preparation device, by means of the same beam source and/or the same radiation detector.

In one embodiment, the spectrometer comprises an analysis window. In particular, "analysis window" means a window in the housing of the spectrometer that is largely permeable for the excitation radiation and/or the measuring radiation provided for analysis. Preferably, the analysis window is made from glass and/or biocompatible.

Another aspect of the present disclosure relates to a system comprising a spectrometer and a control device. In particular, the spectrometer is the spectrometer according to the aspect of the present disclosure described in the introduction. The control device is configured such that a nutrient, a nutrition component, an ingredient substance or a state is identified by means of analysis information, which is provided by the spectrometer, from an analysis of a food or food component. A particularly high degree of automation and ease of use are thus obtained. In one embodiment, the control device is located in the spectrometer, for processing and, optionally, evaluating the measurement signals from the radiation detector. The spectrometer can thus be operated particularly autonomously and independently of other devices, and indicate an analytical result to the user, for example. In an alternative or additional embodiment, the control device is located in a food preparation device or in a computer, which is accessible via a network and in particular via the internet, for evaluating the analysis information, such as a measurement signal from the spectrometer that has not yet been evaluated. Hereinafter, such a remote computer, which is preferably accessible via the internet, is also referred to as a cloud computer. Thus, complicated electronic systems can be omitted in the spectrometer. Thus, the spectrometer can be made particularly light, easy to handle and with little production expenditure. When outsourcing the control device into a cloud computer, spectral fingerprints are, in one embodiment, centrally managed in the form of stored reference values and/or data sets, i.e. for more than one user or for more than one spectrometer or system. Optionally, evaluation algorithms may also be centrally stored and managed in the cloud. Constant optimizations and add-ons from the manufacturer are thus made possible.

In one embodiment, the control device comprises a processor unit and a storage unit. In particular, the control device is configured such that a method can be carried out using the processor unit, preferably based on a computer program or commands stored in the storage unit. In particular, a method includes steps for executing an evaluation algorithm. In particular, a spectral fingerprint and/or an evaluation algorithm are stored in the control device, i.e. digitally stored in the storage unit. The, in particular, analog and/or digital measurement signals of the spectrometer and, optionally, analytical results of the spectrometer can be processed by the control device.

Preferably, signal preprocessing and/or signal correction, e.g. for compensating a temperature influence or for analog/digital conversion, are being carried out before the preprocessed measurement values thus obtained are analyzed using the stored data, particularly while applying the predefined evaluation algorithm. In particular, the signal preprocessing takes place in the spectrometer.

In one embodiment, a spectral fingerprint stored in the form of a data set, in particular in the storage unit of the control device, is used for identifying a nutrient, nutrition component, ingredient substance or state. Preferably, this data set, for one or more predefined wavelengths of the measuring radiation, respectively includes a predefined intensity threshold or a predefined intensity range. If a comparison of the measuring radiation to the data sets shows that the conditions of a certain data set are met by the measuring radiation, the nutrient, nutrition component or the food, ingredient substance or state of the food or food component of the recognized spectral fingerprint or of the correspondingly assigned data set is outputted as the analytical result.

In particular, an analytical result may be a browning level, an alcohol concentration, a water content, a cocoa content in a chocolate, a gluten content in flour, a main nutrient content or an energy content. The analytical result may be both a qualitative presence of an ingredient substance and its quantitative concentration. The identification of a food component, e.g. "apple", is also possible. In particular, a particularly precise analysis can be achieved by means of a database comparison or by taking into account the recipe or the cooked food, wherein this information can be outputted to the control device, for example, by a food processor or a smartphone.

In one embodiment, the control device receives data from the food preparation device and/or transmits control signals to the food preparation device. Data may include recipe information, a temperature of the food or in the food preparation space of the food preparation device measured by the food preparation device, or other analog or digital data available to the food preparation device. Generally, transmission may take place through a cable or wirelessly. A control signal serves for controlling a functional component, such as a heating element or revolving motor for the tool of the food preparation device. In principle, a computer program of the food preparation device may also be activated by a control signal. A particularly precise analysis of a food can be achieved by obtaining data from the food preparation device and/or transmitting a control signal. A precise analysis of the food can be further improved by, for example, taking into account the recipe. A process monitoring or process control of the cooking process of the food preparation device can be made possible.

Since there are frequently elevated temperatures during the preparation process, for example, which are also reflected in an amount of infrared radiation, a temperature measurement is provided in one embodiment, which is preferably carried out by an existing temperature sensor of, for example, a food processor or oven, which is also provided for other purposes. The influence of the temperature can then be eliminated, e.g. by means of its Planck curve, within the context of signal processing.

In one embodiment, the food preparation device is included in the system and/or the control device is configured such that a preparation process of a food carried out by the food preparation device is monitored or controlled by means of the analysis information. In this way, a particularly reproducible cooking result and/or particularly exact knowledge about the nutritional value of the food that is actually being prepared can be made possible. Based on the actually added food components prior to preparation and/or the actual state of the food during preparation, it is possible in one embodiment, for example, to monitor the process and optimize the preparation process by controlling individual cooking parameters, such as temperature and time, or by requesting the user to add a certain food component, such as sugar or water. Subsequent to preparation, main nutrients, i.e. carbohydrates, fat and protein can be determined and the energy content of the prepared food in kilocalories (kcal) can be calculated in order to compare them with a stored diet plan, which is preferably stored in the food preparation device. In one embodiment, the spectrometer and/or a food processor are connected to an oven for exchanging data in order to be able to provide cross-device functions.

Another aspect of the present disclosure relates to a method for analyzing a food, wherein a spectrometer analyzes the food or a food component of the food prior to, during and/or subsequent to a preparation of the food, wherein the preparation of the food is carried out by means of a food preparation device and/or the spectrometer is connected to the food preparation device for transmitting information, i.e. sends information to the food preparation device and/or receives information from the food preparation device. A desired food can be prepared particularly conveniently by this method. Precise knowledge about a self-prepared food can be obtained and a reproducible cooking result can be made possible. In particular, the spectrometer is the spectrometer according to the aspect of the present disclosure described in the introduction, so that the above-described features and embodiments can be combined with the method.

Another aspect of the present disclosure relates to a method for analyzing a food, wherein the food or a food component or component of the food is analyzed by means of a spectrometer prior to, during and/or subsequent to a preparation of the food, wherein the preparation of the food is carried out by means of a food preparation device comprising a food preparation space and a heating element for heating a food in the food preparation space and/or a tool for blending and/or chopping a food in the food preparation space. In particular, the food preparation device is the food preparation device according to the aspect of the present disclosure described in the introduction, so that the above-described features and embodiments can be combined with the method.

Exemplary embodiments of the present disclosure will be explained below in more detail with reference to Figures. Disclosed features may be combined in any way with the subject matters for which protection is sought. The claimed scopes of protections are not limited to the exemplary embodiments.

BRIEF DESCRIPTIONS OF THE DRAWINGS

Figure 2:
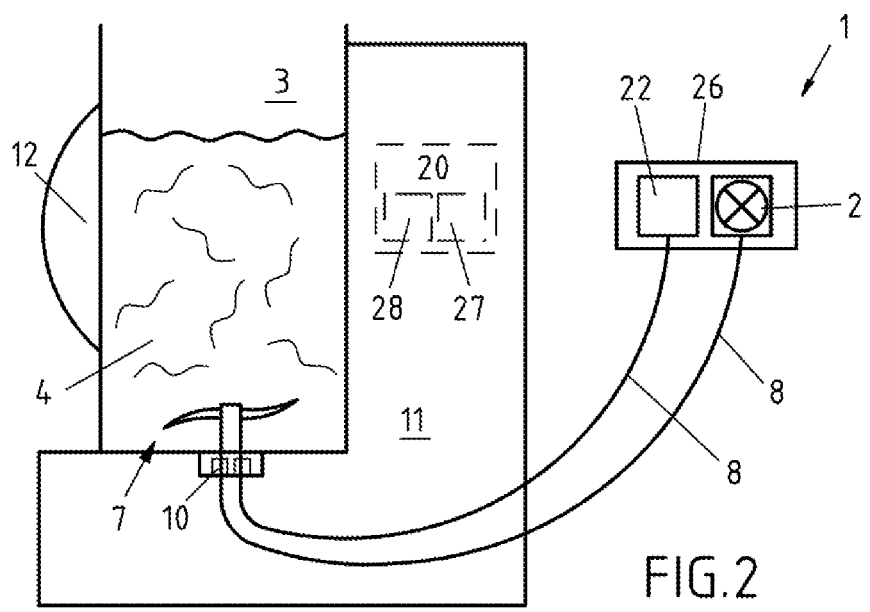
Figure 3:
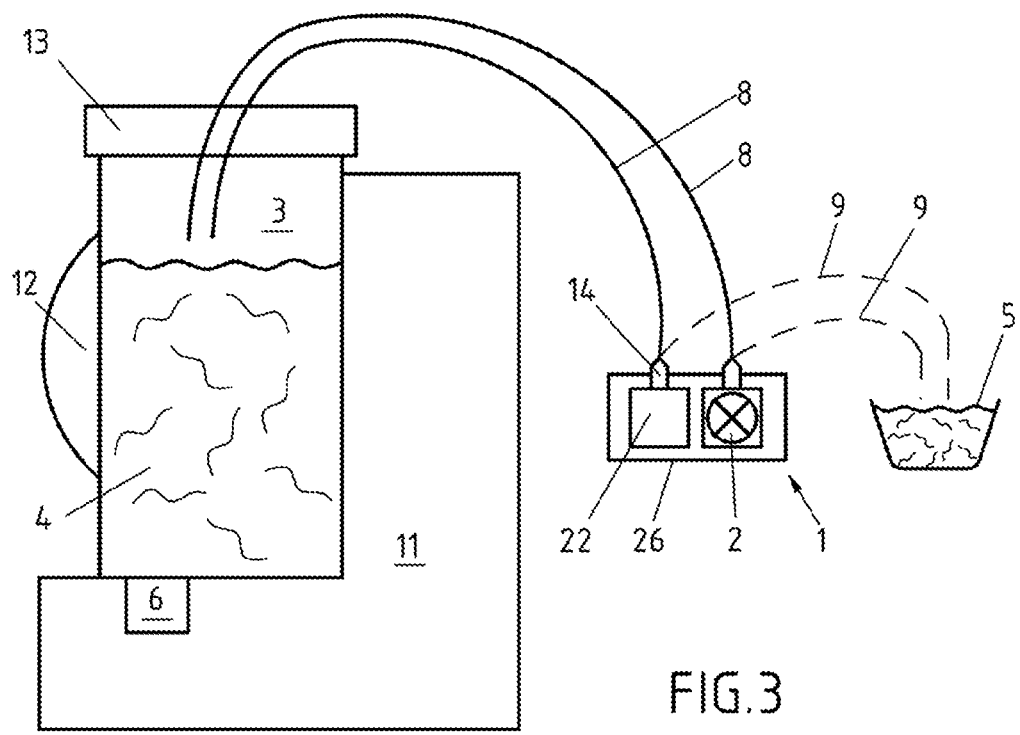
Figure 4:
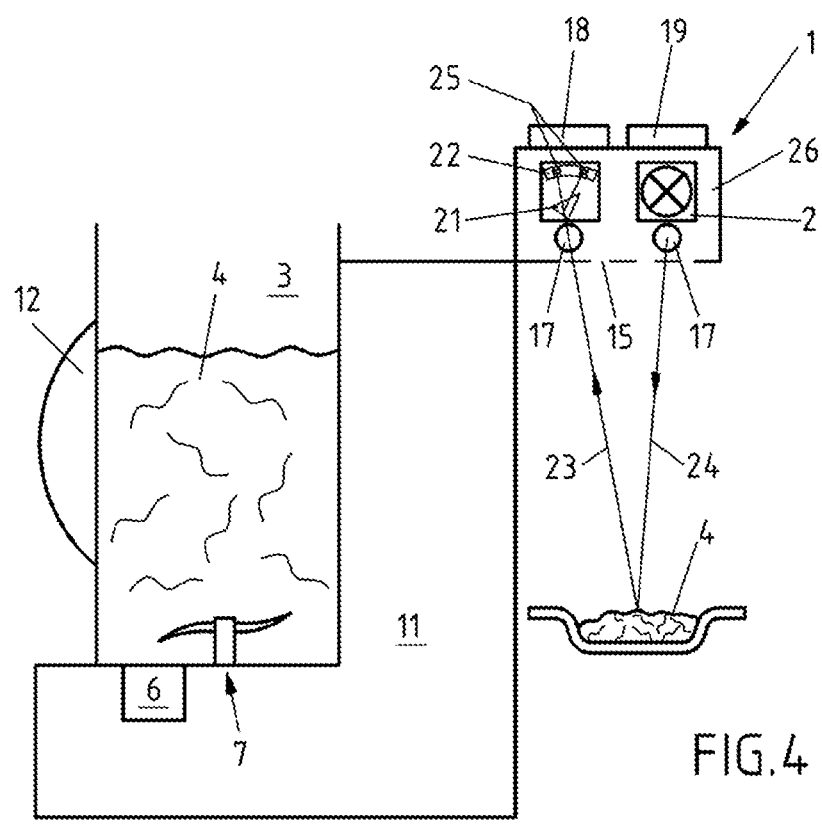

In the Figures:

FIG. 1: shows a schematic representation of an encapsulated spectrometer;

FIG. 2: shows a schematic representation of a spectrometer that can be coupled to a tool of a food preparation device;

FIG. 3: shows a schematic representation of a spectrometer with flexibly usable optical fibers; and FIG. 4: shows a schematic representation of a spectrometer for the analysis of a food prepared with a food preparation device.

DETAILED DESCRIPTION

FIG. 1 shows a portable spectrometer 1, which is encapsulated by a watertight housing 26, with a beam source 2 and a radiation detector 22. The illustrated spectrometer 1 is able to float, and not sink, in a low-viscosity food 4, e.g. a soup. In one embodiment, the spectrometer 1 can therefore be placed in the food preparation space 3, together with ingredients, prior to or during the preparation of the food 4. In particular, it is intended that the spectrometer 1 floats alongside, on top of or in the food in the case of liquid foods 4. The food 4 can be heated in FIG. 1 by a heating element 6.

A data interface 16 is provided for wirelessly transmitting analysis information, as shown in FIG. 1, to a cloud or a food preparation device 11, 12, such as a food processor, for example via Bluetooth or wireless LAN.

An exchange of data or information may also be provided for. The spectrometer 1 may include its own control device 20 for carrying out an analysis and outputting an analytical result. For example, a warning signal may be outputted via an integrated speaker if a predefined target state stored in the storage device 20, such as an acidity, has been reached. In principle, a measurement signal and/or analytical result may also be outputted via the data interface 16. In FIG. 1, the food preparation space 3 is provided by a container 12 of the food preparation device 11, 12, whose basic device 11 accommodates the container 12. In particular, another control device 20 may be integrated into the basic device 11 of the food preparation device 11, 12 (not shown in FIG. 1). In that case, the spectrometer 1 sends the analysis information to it.

FIG. 2 shows a spectrometer 1 in which the beam source 2 and the radiation detector 22 can each be connected to optical fibers 8 in order to be optically coupled and connected to a food preparation device 11, 12 via a coupling interface 10. In particular, the spectrometer is thus capable of introducing excitation radiation through a tool 7 for blending and/or chopping into a food 4 during preparation, and of receiving measuring radiation for the analysis of the food 4 from it. Preferably, the food preparation device 11, 12 is capable of exchanging data with the spectrometer 1 which, in one configuration, can be realized in all systems of the FIGS. 1 to 4. A dynamic adaptation and/or control of the preparation parameters, such as temperature, cooking time or rotation speed of the tool 7 can thus be realized particularly reliably, depending on the identified food components, the currently present ingredient substances and the actual state of the food. Furthermore, a dynamic adaptation of the list of ingredients can be carried out and indicated to the user during the preparation if a lack or excess of a specific ingredient substance is detected. A particularly optimized and/or reproducible cooking result can thus be made possible in spite of variable quality and quantity of the initially added food components, i.e. foodstuffs or ingredients, and changes to the food components during preparation, e.g. due to evaporation or fermentation. A destructive or, especially, invasive analysis can be omitted.

A data set for a spectroscopic fingerprint, an evaluation algorithm and/or predefined monitoring quantities and a target value can be stored in a storage unit 27. A processor unit 28 is capable of carrying out signal preprocessing and/or an evaluation using these data stored in the storage unit.

If a target value of a predefined monitoring quantity has been reached, the food preparation device 11, 12 can take correspondingly predefined measures, which are preferably also stored in the storage unit 27. For example, when cooking or baking, the browning level may be the monitoring quantity, and the desired browning level the target value, so that a heating element 6 is switched off or turned down when the target value has been reached. In one embodiment, food-specific or user-specific stopping or abort criteria are defined. Thus, for example, a cooking process can be stopped if the analysis determines that a predetermined browning level has been reached. This may also be used as a safety function in the distillation of alcohol.

FIG. 3 shows a spectrometer 1 in which optical fibers 8 extend from the spectrometer 1 through a lid 13 into the food preparation space 3 for the analysis of a food prior to, during or subsequent to preparation. Additional optical fibers 9 are in each case connected in parallel thereto by means of optical combiners 14, in each case at the beam source 2 and the radiation detector 22, with which, for example, a food component to be added, i.e. and ingredient, can be analyzed preferably outside the food preparation space 3. In this way, particularly accurate knowledge of the actually used ingredients or food components 5 to be added, and thus the nutritional value of a self-prepared food 4, can be obtained, e.g. for adhering to a diet. In one embodiment, the food 4 or the food components 5 are analyzed in the food preparation space 3 prior to preparation. Thus, the cooking process can be adapted to a variable quantity or quality of the initial state of the food 4 prior to preparation, or of the introduced food components 5, in order to obtain a reproducible or at least optimized cooking result even in the case of changed mixing ratios, recipe changes or foods prepared without a recipe.

FIG. 4 shows a portable spectrometer 1, in particular having the approximate shape and size of a TV remote control. The spectrometer 1 can be handled and operated using only one hand. An operating switch 18 is disposed next to an output device 19 for outputting analysis information. In particular, the output device 19 is a display or touchscreen. Alternatively or additionally, the output device 19 may be an SD card interface or a USB interface. The spectrometer 1 has a length of 150 to 200 mm, a width of 50 to 120 mm, and a depth of 10 to 30 mm. Preferably, an automatic dark calibration takes place subsequent to activation.

In one embodiment, the spectrometer 1 can be mechanically coupled to an oven, a container 12, a lid 13 or a basic device 11. In that case, the user is able to manually mechanically couple or detach the spectrometer 1. In the coupled state, it is preferably possible to fix the orientation so as to be able to carry out an analysis of the preparation process with the spectrometer 1 even if the user is absent. Monitoring or controlling the preparation process can thus be carried out particularly conveniently with the portable spectrometer 1.

In one embodiment, a focusing and/or a moving device 17 are provided, so that an excitation radiation 24 can be flexibly directed towards a food 4 and/or a measuring radiation 23 from a food 4 can be flexibly captured. "Flexible" means from a different position, under a different angle or with a different focus setting or focal length. In particular, the moving device is a motor-operated deflection mirror. In particular, the focusing device comprises a lens system. In particular, one analysis window 15 is in each case provided on an input of the radiation detector 22 and/or an output of the beam source 2. Preferably, the focusing and/or moving device 17 is optically connected or optically coupled to the input and/or output.

FIG. 4 shows how the excitation radiation 24 is directed from the beam source 2 onto prepared food 4 located on a plate. The food, in turn, emits a measuring radiation 23, which may be a reflected component of the excitation radiation 24. In turn, the spectrometer 1 captures this measuring radiation 23. Using the spectral decomposition device 21, the measuring radiation 23 is diverted in different directions depending on the wavelength and is thus incident on different areas of the radiation detector 22. Several detector units 25 are placed at such areas, upon which a component of the measuring radiation 23 is incident with an especially high intensity or a peak intensity if a certain food component, nutrient, nutrition component, ingredient substance or state is present.

In one embodiment, the analytical result is outputted to the user by a food processor, and thus by a food preparation device 11, 12. For example, it may be provided that, depending on the analytical result, a recommendation is outputted to the user depending on the recipe. If, for example, the sugar level recommended for a particular flavor has not yet been reached due to ingredients that are too sour, sweetening can be recommended to the user. Alternatively or additionally, the analytical result is outputted to the user by the spectrometer 1, visually, acoustically or by means of a transmission to an external device, such as a smartphone.

The invention claimed is:

1. A spectrometer comprising:
a beam source for emitting an excitation radiation with a wavelength between 780 nm and 3000 nm on a food,
a spectral decomposition device, and
a radiation detector, wherein the spectral decomposition device is configured to receive an incident electromagnetic measuring radiation generated in response to the excitation radiation being reflected by the food, wherein the spectral decomposition device is configured to break up the incident electromagnetic measuring radiation, into a plurality of components having different wavelengths, wherein the spectral decomposition device is configured to divert each component in a different direction based on the wavelength,
wherein the radiation detector includes at least two photodiodes for receiving different components of the plurality of components from those of one another and converting intensities of the received components into measurement signals correlating with the intensities,
wherein the radiation detector does not comprise a charge-coupled device (CCD) sensor or a pixel of the CCD sensor,
wherein the at least two photodiodes receive components having intensities within different intensity thresholds or intensity ranges, wherein the intensity thresholds or intensity ranges correspond to spectral fingerprints defined by respective data sets stored in a storage unit, wherein each fingerprint is defined by one data set which includes at least a first wavelength and a first intensity threshold or intensity range, and a second wavelength and a second intensity threshold or intensity range,
wherein the at least two photodiodes are separate and independent of one another and can be positioned independently and fixed at such predefined positions so as to receive only the components having wavelengths contained in the data sets of the corresponding spectral fingerprints,
wherein the at least two photodiodes are positioned at such locations of the radiation detector at which a component of the measuring radiation is respectively incident, whose wavelength, in connection with an intensity threshold or an intensity range, defines a spectroscopic fingerprint for a certain food component, nutrient, nutrition component, ingredient substance or state, and
wherein the spectrometer is configured to transmit at least one piece of analysis information from the analysis of a food to a food preparation device or output the at least one piece of analysis information to a user via an output device.

2. The spectrometer of claim 1, wherein the spectrometer is portable.

3. The spectrometer of claim 2, wherein the spectrometer is encapsulated.

4. The spectrometer of claim 1, further comprising a beam source configured to emit an excitation radiation near the infrared range.

5. The spectrometer of claim 1, wherein the spectrometer includes an optical coupling interface configured to couple to an optical fiber.

6. The spectrometer of claim 5, further including an optical combiner configured to guide an excitation radiation through the optical fiber and a second optical fiber.

7. The spectrometer of claim 5, further including an optical combiner configured to guide the measuring radiation through the optical fiber and a second optical fiber.

8. The spectrometer of claim 1, wherein the beam source is configured to emit the excitation radiation having a wavelength in an infrared range.

9. The spectrometer of claim 8, wherein the radiation detector includes up to thirty separate detector units.

10. The spectrometer of claim 1, wherein the spectrometer includes an optical coupling interface configured to couple to an optical fiber.

11. The spectrometer of claim 1, wherein the spectral decomposition device is an optical device comprising at least one of a prism, a grating, or an interferometer, and the optical device is configured to divert an electromagnetic measuring radiation into a plurality of directions depending on the wavelength so that a first component of the measuring radiation with a first wavelength hits a first area of the radiation detector, and a second component of the measuring radiation with a second wavelength differing from the first wavelength hits a second area of the radiation detector,
wherein a first detector unit is fixed at the first area and a second separate detector unit is fixed at the second area.

12. The spectrometer of claim 1, further comprising a mechanical coupling interface at a side of the spectrometer that enables a user to couple the spectrometer to a kitchen appliance such that the excitation radiation is emitted through an analysis window at the bottom side of the spectrometer to food below the spectrometer and to capture the reflected measurement radiation that enters the spectrometer also though said analysis window.

13. The spectrometer of claim 1, wherein the space separating the two separate photodiodes is at least twice as large as one of the two separated photodiodes.

14. The spectrometer of claim 1, wherein the spectrometer comprises less than thirty photodiodes, which are not arranged side-by-side and which are not arranged with an uniform distance between one another.

15. A method for analyzing a food, the method comprising:
emitting, by a spectrometer, an excitation radiation with a wavelength between 780 nm and 3000 nm on a food;
capturing, using a radiation detector of the spectrometer, an incident electromagnetic measuring radiation generated in response to the excitation radiation being reflected from the food or a food component,
breaking up the incident electromagnetic measuring radiation into a plurality of components having different wavelengths and diverting each component in a different direction based on the wavelength, wherein the radiation detector includes at least two detector units for receiving different components of the plurality of components from those of one another and converting intensities of of the received components into measurement signals correlating with the intensities, wherein the spetrometer radiation detector does not comprise a charge-coupled device (CCD) sensor or the a pixel of the CCD sensor,
wherein the at least two detector units receive components having intensities within different intensity thresholds or intensity ranges, wherein the intensity thresholds or intensity ranges correspond to spectral fingerprints defined by respective data sets stored in a storage unit, wherein each fingerprint is defined by one data set which includes at least a first wavelength and a first intensity threshold or intensity range, and a second wavelength and a second intensity threshold or intensity range, wherein the at least two detector units are separate and independently independent of one another and can be positioned independently and fixed on the radiation detector only at such predefined positions so as to receive only that arc hit by a component the components of the measuring radiation, which has a wavelength having wavelengths contained in the data sets of the corresponding spectral fingerprints, wherein the at least two detector units are positioned at such locations of the radiation detector at which a component of the measuring radiation is respectively incident, whose wavelength, in connection with an intensity threshold or an intensity range, defines a spectroscopic fingerprint for a certain food component, nutrient, nutrition component, ingredient substance or state, and analyzing the food using the spectrometer based on the detected components of the measuring radiation, and transmitting at least one piece of analysis information from the analysis of a food to a food preparation device.

* * * * *